US005731291A

United States Patent [19]
Sullivan et al.

[11] Patent Number: 5,731,291
[45] Date of Patent: Mar. 24, 1998

[54] PARTIALLY LYOPHILIZED FRUCTOSE-1,6-DIPHOSPHATE (FDP) FOR INJECTION INTO HUMANS

[75] Inventors: Brian W. Sullivan, Escondido; Paul J. Marangos, Encinitas, both of Calif.

[73] Assignee: Cypros Pharmaceutical Corp., Carlsbad, Calif.

[21] Appl. No.: 705,773

[22] Filed: Aug. 30, 1996

Related U.S. Application Data

[63] Continuation-in-part of Ser. No. 646,600, May 8, 1996.
[51] Int. Cl.$^6$ ..................................................... A61K 31/70
[52] U.S. Cl. ........................................................ 514/23
[58] Field of Search ........................................... 514/23

[56] References Cited

U.S. PATENT DOCUMENTS

| | | | |
|---|---|---|---|
| 4,530,902 | 7/1985 | Perri et al. | 435/105 |
| 4,546,095 | 10/1985 | Markov | 514/23 |
| 4,575,549 | 3/1986 | Diana et al. | 536/117 |
| 4,703,040 | 10/1987 | Markov | 514/23 |
| 4,870,057 | 9/1989 | Chiapparelli et al. | 514/23 |
| 5,039,665 | 8/1991 | Markov | 514/23 |
| 5,094,947 | 3/1992 | Nakajima et al. | 435/105 |
| 5,434,255 | 7/1995 | Katayama et al. | 536/117 |
| 5,506,210 | 4/1996 | Parish et al. | 516/23 |
| 5,516,526 | 5/1996 | da la Torre | 424/449 |
| 5,571,906 | 11/1996 | Ceccarelli et al. | 536/117 |

FOREIGN PATENT DOCUMENTS

| | | | |
|---|---|---|---|
| 1089615 | 7/1994 | China | C07H 1/06 |
| 1089616 | 7/1994 | China | C07H 11/04 |
| 1089654 | 7/1994 | China | C12N 1/18 |
| 3323850 | 1/1985 | Germany | A61K 31/70 |

OTHER PUBLICATIONS

Chemical Abstracts 124: 56553 (1993). Ouyang et al.
WPIDS 133439 (1989). Cavicchia et al.
Angelos, M.G., et al, "Fructose-1, 6–diphosphate fails to limit early myocardial infarction size in a canine model," *Ann. Emerg. Med.* 22: 171–177 (1993).
Brunswick, R., et al, "Preservation of myocardium by infusion of fructose diphosphate following coronary occlusion," abstract, *Am J Cardio* 49: 1008 (1982).
Cargnoni, A., et al, "Role of timing of administration in the cardioprotective effect of fructose–1, 6–bisphosphate," *Cardiovasc Drugs Ther* 6: 209–217 (1992).
Conti, V.R., et al, "Metabolic and functional effects of carbohydrate substrate with single–dose and multipledose potassium cardioplegia," *Ann. Thoracic Surg.*36: 320–327 (1983).
de la Torre, J.C. "Treatment of head injury in mice, using a fructose 1,6–diphosphate and dimethyl sulfoxide combination," *Nuerosurgery* 37; 273–279 (1995).
Eddy, L.J., et al, "Lack of a direct metabolic effect of fructose, 1,6–disphosphate in ischemic myocardium," *Am J Physiol* 241: H576–583 (1995).

"Esafosfina" sales brochure (Biomedica Foscama: Ferentino, Italy.
Farias, L.A., et al, "Effects of fructose–1, 6–diphosphate, glucose and saline on cardiac resuscitation," *Anesthesiology* 65: 595–601 (1986).
Granot, H., et al, "Successful treatment of irreversible hemorrhagic shock in dogs with fructose–1,6 diphosphate and dichloroacetate," *Circ Shock* 163–173 (1985).
Haasinen, I.E., et al, "Mechanism of the effect of exogenous FDP on myocardial energy metabolism."*Circulation* 83: 584–593 (1991).
Lazzarino G., et al, "Proctective effects of exogenously administered fructose–1,6–diphosphate from ischemia reperfusion damage induced on isolated rat heart,"*Ital J Biochem* 38: 251A–253A (1989).
Lazzarino, G., et al, "Ischemia and reperfusion: effect of fructose–1,6–bisphosphate,"*Free Radic Res Commun* 16; 325–339 (1992).
Marchionni, N., et al, "Hemodynamic and electrocardiographic effects of fructose–1,6–diphosphate in acute myocardial infarction," *Am J Cardiol* 56: 266–269 (1985).
Markov, A.K., et al, "Prevention of arrhythmias with fructose disphosphate in acute myocardial ischemia," abstract, *Circulation* 62: III–143 (1980).
Markov, A.K., et al, "Hemodynamic, electrocardiographic, and metabolic effects of fructose diphosphate on acute myocardial ischemia," *Am Heart J* 100: 639–646 (1980).
Markov, A.K., "Hemodynamic, and metabolic effects of fructose 1–6 diphosphate in inschemia and shock—experimental and clinical observations," *Ann Emerg Med* 15: 1470–7 (1986).
Markov, A.K., et al, "Increasing survival of dogs subjected to hemorrhagic shock by administration of fructose 1–6 diphosphate," *Surgery* 102: 515–527 (1987).

(List continued on next page.)

*Primary Examiner*—Zohrey Fay
*Attorney, Agent, or Firm*—Patrick D. Kelly

[57] ABSTRACT

A method is disclosed for preparing a partially lyophilized (freeze-dried) powder or solidified cake containing fructose-1,6-diphosphate (FDP), a naturally-occurring intermediate in glycolysis. Preferably, about 10% to 25% residual water (by weight) is left in the powder or cake. This high moisture content does not degrade or limit FDP's stability or shelf life, and it provides for faster, less expensive processing. The methods disclosed herein also allow direct lyophilization inside a vial or other sealed container that will hold the lyophilized FDP, to avoid any need for milling, handling, or other treatment under conditions that might endanger its sterility. Lyophilized FDP can be used to create emergency injection kits which also contain aqueous solutions for mixing, and syringes and needles for injection. These kits can be carried in ambulances, police cars, firetrucks, etc., and can be stored at nursing homes, swimming pools, and in the homes of people suffering from various conditions such as heart disease or sicle cell anemia. These kits will allow rapid (even pre-diagnostic) injection of FDP into people suffering medical crises such as heart attacks, severe blood loss, suffocation, etc.

18 Claims, 6 Drawing Sheets

OTHER PUBLICATIONS

Mouchawar, A., et al, "A pathophysiological approach to the patient in shock, " *Int Anesthesiol. Clin.* 31: 1–20 (1993).

Pasque, M.K., et a, "Metabolic intervention to affect myocardial recovery following ischemia,"*Annal of Surgery* 200: 1–12 (1984).

Sernov, L.N., et al, "The characteristics of the cardioproctective action of fructose–1,6–diphosphate," *Biull Eksp Biol Med* 111: 172–173 (1991) (abstract).

Sernov, L.N., et al, "The antiacidotic and cardioprotective effects of fructose–1,6–diphosphate and dehydroascorbic acid," *Farmakol Toksikol* 54: 24–26 (1991) (abstract).

Sernov, L.N., et al, "A comparative evaluation of the cardioprotective and antianginal actions of energy–providing agents," *Eksp Klin Farmakol* 55:13–15 (1992) (abstract).

Stryer, L., *Biochemistry,* 2nd ed., pp. 266–267 (Freeman & Co., San Francisco, 1981).

Tortosa, A., et al, "Fructose–1,6–bisphosphate fails to ameliorate delayed neuronal death in the CA1 area after transient forebrain ischaemia in gerbils," *Neuropharmacology* 32: 1367–1371 (1992).

Zhang, J.N., et al, "Protective effect of exogenous fructose–1,6–disphosphate in cardiogenic shock," *Cardiovasc Res* 22: 927–932 (1988).

PARTIALLY LYOPHILIZED FRUCTOSE-1,6-DIPHOSPHATE (FDP) FOR INJECTION INTO HUMANS

RELATED APPLICATION

This application is a continuation-in-part of U.S. patent application Ser. No. 08/646,600, filed on May 9, 1996.

BACKGROUND OF THE INVENTION

Glycolysis is a fundamental biological process which is essential to the generation and use of energy by cells. In this process, a molecule of glucose (a 6-carbon sugar) is broken apart to form 2 molecules of pyruvic acid, containing 3 carbons each, in a series of ten distinct reactions which are controlled by enzymes. In subsequent reactions, pyruvate is converted into carbon dioxide and water, if enough oxygen is present in the cells, via the Krebs cycle. In cells that do not have enough oxygen, pyruvate is converted into lactic acid, via a different pathway. Glycolysis is discussed in detail in nearly any textbook on biochemistry, physiology, or cell biology; see, e.g., any edition of Stryer's or Lehninger's *Biochemistry*, Guyton's *Medical Physiology*, or Alberts et al, *Molecular Biology of the Cell*.

Fructose-1,6-diphosphate (FDP) is a naturally occurring sugar-phosphate molecule, which is created and then quickly consumed as an intermediate during the series of reactions that make up glycolysis. As a short-lived intermediate that is quickly consumed, it normally is present in cells only at relatively low concentrations. It should be noted that some scientists refer to FDP as fructose-1,6-biphosphate, or fructose-1,6-bisphosphate.

The 1,6-isomer of fructose diphosphate, which contains phosphate groups bonded to the #1 and #6 carbon atoms of the fructose molecule, is the only isomer of interest herein. Other isomers (such as fructose-2,6-diphosphate) are not relevant herein, and are excluded from any references herein to FDP or fructose diphosphate.

Numerous medical and scientific articles have suggested that FDP might potentially be useful as a medical treatment for patients and victims suffering from medical crises such as strokes, cardiac arrest, heart attack, suffocation, loss of blood due to injury, shooting, or stabbing, etc. Such articles include Markov et al 1980, 1986, and 1987, Brunswick et al 1982, Marchionni et al 1985, Granot et al 1985, Farias et al 1986 and 1989, Grandi et al 1988, Zhang et al 1988, Cacioli et al 1988, Lazzarino et al 1989, Crescimanno et al 1990, Gregory et al 1990, Farias et al 1990, Janz et al 1991, Nakai et al 1991, Hassinen et al 1991, Bickler et al 1992, Lazzarino et al 1992, Cargnoni et al 1992, Kuluz et al 1993, Trimarchi et al 1993 and 1994, Gobbel et al 1994, Hardin et al 1994, Munger et al 1994, Kelleher et al 1994 and 1995, de la Torre 1995, and Sano et al 1995. Relevant U.S. patents include U.S. Pat. No. 4,546,095 (Markov 1985), U.S. Pat. No. 4,703,040 (Markov 1987), and U.S. Pat. No. 4,757,052 (Markov 1988).

Despite all of these published articles and patents, which stretch back to at least 1980, a high degree of skepticism and reluctance still exists regarding FDP use to treat ischemia or hypoxia. Except for a few small and very limited clinical trials, FDP simply is not used or prescribed by any practicing physicians, except possibly in a few foreign countries such as China and Italy.

The absence of actual use of FDP on patients (many of whom desperately need the energy supplies that could be derived from FDP, as they are dying of massive heart attacks, cardiac arrest, strokes, or blood loss) is believed to be due to a number of factors, including the following:

(1) FDP is a diphosphate with a strong negative charge, and it is generally assumed by doctors and researchers that its highly-charged nature will prevent it from entering cells in substantial quantities. Since energy metabolism and glycolysis occur inside cells, it is generally assumed that FDP will not get to the relevant site in sufficient quantities to do any substantial good.

(2) It is also believed that FDP has a very short half-life in the blood, and will effectively disappear from the blood within a few minutes after injection or infusion.

(3) The amount of energy generated during glycolysis (i.e., the conversion of glucose to pyruvic acid) is only a small fraction of the energy generated by the aerobic (Krebs Cycle) oxidation of pyruvic acid to form carbon dioxide and water. Therefore, under conditions of tissue ischemia or hypoxia, where an oxygen deficit blocks aerobic conversion, it is generally assumed that FDP infusion would be insufficient to supplement ATP levels to a degree that can significantly aid cell survival.

(4) As a corollary to the above, it is generally assumed that under conditions of ischemia or hypoxia, where inadequate oxygen is present, an injection of FDP would likely lead to increases in lactic acid levels. This would be harmful, rather than beneficial.

(5) It is also generally believed that FDP cannot penetrate the blood-brain barrier in significant quantities, and therefore offers little or no benefit in protecting the brain or spinal cord against neuronal death and damage caused by stroke, head injuries, or other problems that generate ischemia in the brain (including stroke, cardiac arrest, hemorrhage or blood loss, etc). Since the brain is much more sensitive and vulnerable to damage by ischemia or hypoxia than any other organ, there is a general assumption that if the first people on the scene can't help protect a patient's brain against ischemic or hypoxic damage, then any benefits that might be offered by FDP injections to other organs, such as the heart, would merely be marginal and minor, and could not address or help solve the critical problem of rapid brain damage.

(6) Drug intervention in acute ischemic trauma has proven to be extremely difficult and complex, for a large number of reasons. Among other things, it often requires 1 to 3 hours (or more) before a patient can be properly diagnosed in a manner that justifies the use of a specific drug. However, if that much time elapses before drug administration, it is often too late to intervene effectively because extensive cell death and permanent tissue damage have already occurred.

(7) Contrary to the articles (cited above) which report that FDP may have beneficial effects in certain types of lab tests, a number of other articles have reported that FDP had no beneficial effects in other studies. Examples of these negative articles include Eddy et al 1981, Pasque et al 1984, Tortosa et al 1993, and Angelos et al 1993.

For these and other reasons, it appears that little if any effort has been directed by the pharmaceutical industry toward developing FDP as a useful drug. Under the laws enforced by the U.S. Food and Drug Administration, FDP cannot be sold in the United States for administration to human patients by physicians. As noted above, with the possible exception of a few small clinical trials, FDP simply is not administered to any patients, on any sort of routine basis, regardless of how desperate their plight may be following a stroke, cardiac arrest, shooting, stabbing, etc.

Currently, there are only two known preparations of FDP which are commercially available anywhere in the world, other than research reagents that are sold in gram or milligram quantities by specialty chemical companies. One of these preparations is a non-sterile bulk powder, manufactured in Germany by Boehringer Mannheim. This material was purchased by the assignee (Cypros Pharmaceutical Corporation, of Carlsbad, Calif.) and used as the starting reagent for the lyophilized preparation described herein.

The other commercially available FDP formulation is a lyophilized preparation that is manufactured in Italy by a company called Biochemica Foscama. To the best of the Applicant's knowledge and belief, it is manufactured by steps that including the following: (1) pouring a large batch of an aqueous mixture of FDP into a large, flat tray; (2) freezing the mixture and subjecting it to a vacuum, to remove the water, thereby creating a large solidified cake; (3) grinding or milling the large cake into small particles; (4) loading the ground-up particles into small vials; and, (5) sealing the vials.

This process is not well suited for creating a sterile preparation, for injection into humans. For example, a manufacturing process which uses large machinery to handle and manipulate a large, flat cake, pass it through a device which grinds it up into small particles, pass the particles through various routing and funnelling devices in order to load those particles into small vials, and then seal the vials, creates numerous risks which seriously jeopardize the sterility of the resulting final product.

It should also be noted that a lyophilized preparation of FDP in a sealed vial cannot be treated by a "terminal sterilization" process; i.e., non-sterile FDP cannot be placed in a vial which is then sealed, and subsequently subjected to a sterilizing step, such as autoclaving or ionizing radiation. Those types of terminal (post-sealing) sterilization treatments would seriously degrade the chemical quality of the FDP in the sealed vials.

The final product of the lyophilized FDP preparation from Biochemica Foscama suffers from several apparent shortcomings. It is relatively inhomogeneous, and contains particles of various different sizes; some appear to be small glass-like beads, while others appear to be relatively sticky, caramelized agglomerations. It is also relatively unstable; while pure FDP is a crystalline white powder, some of the particles in the Biochemica Foscama preparation (especially the larger particles) begin to turn a yellowish-brown color within a few days or weeks, when stored at room temperature, unopened, in the sealed vials.

To the best of the Applicant's knowledge and belief, neither the Boehringer Mannheim company (headquartered in Germany) nor the Biochemica Foscama company (located in Italy) have ever made any effort to obtain permission from the U.S. Food and Drug Administration to sell their FDP preparations in the United States, for use on humans.

Lyophilization

Lyophilization is the technical name for a process often referred to as "freeze-drying". In this process, an aqueous mixture or suspension is frozen into a solid, then it is subjected to a vacuum for a substantial period of time (usually a full day or more). The vacuum causes the water molecules to "sublimate", i.e., to become gaseous and leave the solid, without going through a liquid state. This is comparable to the evaporation of carbon dioxide from "dry ice", but it is much slower, and it requires high levels of vacuum, which can only be generated in a special and expensive type of lyophilization chamber which can generate and sustain both (1) very cold freezing temperatures, which are much lower than the typical temperatures of conventional household freezers, and (2) very high levels of vacuum, measured in millitorr (thousandths of a torr; typical atmospheric pressure is 760 torr, or 760 millimeters of mercury column in a U-shaped device called a manometer).

Because of the extremely high requirements for sterility and quality control, lyophilization of pharmaceuticals is a very expensive process. It requires a lot of energy to sustain the proper freezing and vacuum conditions in a lyophilization chamber, and each batch of drugs must sit in an expensive chamber, absolutely motionless, for many hours or days. For these and other reasons, any processing improvement that can speed up a lyophilization protocol without compromising the quality or sterility of the product is regarded as an improvement over longer, slower processes.

Residual Moisture Levels

One of the most important factors in lyophilizing a drug product is the final water content. Most lyophilization protocols include both a "primary drying" stage, which reduces moisture content to a level of about 7% to 10%, by weight, followed by a "secondary drying" stage, which usually reduces the water content to less than 2%. Reducing residual water content to less than about 2% helps keep hydrolysis (or other chemical reactions that might alter the chemical bonds in the drug molecule) to a minimum.

Relevant prior art which discusses residual moisture content includes the following:

(1) U.S. Pat. No. 4,537,883, which states: "Final moisture content of the dried product is generally below 1.0%, although some products, mainly biologicals, may have a final moisture content which could range as high as about 10%. Usually, the improvement in stability of the lyophilizate, compared to the solution, is due to the absence of water in the pharmaceutical composition."

(2) Adams, G. D. J., *Freeze-Drying of Biological Materials, Drying Technology*, 9(4), (1991), pages 891–925, which states: "The prolonged drying stage is called secondary drying, water being removed by desorption. During secondary drying the water content is reduced to 2% or less."

(3) Greiff, D., "Freeze-Drying Cycles," in *International Symposium on Freeze Drying of Biological Products* (published by S. Karger, Basel, Switzerland, 1977, pp. 105–115): "During the drying process, suspensions will contain biologic materials in at least three states: (1) dried materials containing low contents of residual moisture (3–5%), (2) dried material containing less than 3% residual moisture, and (3) non-dried, frozen material."

(4) A section entitled, "Formulation and Process Guidelines," by Michael J. Pikal and Steven L. Nail, in the printed course notes from *Lyophilization: A Short Course*, sponsored by Parenteral Drug Association, Inc. (Mar. 13–14, 1996), states as follows: "Secondary Drying: . . . The first question is, 'What is the desired level of residual water?' This issue should be addressed during formulation development studies. In many cases, the lower the residual moisture, the more stable is the product. However, there may not be a significant difference in stability between zero water, and some moderate moisture level, such as 1% . . . An optimum level of water which is relatively high (5%) would be difficult, and formulation approaches should be explored in an attempt to circumvent this requirement."

(5) *Guidelines for the Determination of Residual Moisture in Dried Biological Products*, Docket No. 89D-0140, January 1990, issued by CBER (the Center for Biologicals Evaluation and Research), which is part of the U.S. Food and Drug Administration: "Residual moisture has been the term used to describe the low level of surface water, usually from less than 1% to 5%, remaining in a freeze-dried vaccine or other biological product after the bulk of the aqueous solvent has been removed during the freeze-drying (vacuum sublimation) process."

The Applicant is not aware of any commercially available lyophilized drug with a residual moisture greater than 10%. Accordingly, the Applicant's discovery that FDP can be "partially lyophilized", allowing residual water contents to remain at least 10%, and up to about 25%, while retaining excellent stability, would have been very surprising for any type of drug. It was even more surprising for fructose diphosphate, since its two phosphate bonds were expected to be quite vulnerable to hydrolysis.

Stability: The 5% Total and 1% Single Impurity Tests

Another important issue in FDP lyophilization is chemical stability, which is required to sustain chemical purity after periods of storage such as a month or more. The goal of lyophilization is to create FDP preparations that have sufficient chemical stability and shelf life to be medically useful, without suffering serious levels of hydrolysis or other chemical degradation, when stored and handled in sealed vials without refrigeration for periods such as a month or longer. This goal is quantified by establishing "benchmark" tests, so that compliance or noncompliance of any given batch (or any particular manufacturing process) can be evaluated by impartial and objective standards. One such benchmark test that is commonly applied to drugs intended for human use is as follows: a preparation of a candidate drug must not contain more than 5% total impurities, and it also must not contain more than 1% of any single impurity. This standard of purity and stability is referred to herein as the "5% total, 1% single impurity rule".

This standard has been applied, by the U.S. Food and Drug Administration, to all human clinical trials which involve fructose-1,6-diphosphate that have been conducted to date by the Applicant, Cypros Pharmaceutical Corporation. It is used and applied herein, in the text of this application, and in the claims; any reference herein to a "chemically stable" lyophilized preparation of FDP refers to a lyophilized preparation of FDP which meets the "5% total, 1% single impurity rule" after storage for a month (or longer) at room temperature.

As used herein, "chemical degradation" of FDP refers to breakage or rearrangement of any carbon-oxygen or oxygen-phosphorous bond; this includes any loss of a phosphate group from the molecule, and it also includes the process called "caramelization," in which separate molecules become bonded to each other, to form agglomerated molecules.

However, it should be noted that FDP (which is acidic, and which is most stable in a salt form, in any aqueous solution) may ionize or be converted into any particular salt, without losing its stucture (or its metabolic activity as an intermediate in glycolysis). Accordingly, ionization and salt formation are not regarded as chemical degradation; they do not involve breakage or rearrangement of any carbon-oxygen or oxygen-phosphorous bond.

In practice, the 1% requirement (for any single impurity) is the crucial standard. That part of the two-prong impurity standard is almost always violated long before the 5% total impurity requirement is even approached. In FDP, the two phosphate bonds are highly susceptible to hydrolysis (i.e., water-induced cleavage). Accordingly, either or both of the phosphate groups will leave the FDP, generating fructose or fructose monophosphate. The remaining phosphate groups are attached to either the #1 or #6 carbon atoms, usually in roughly equal proportions. Either form of fructose monophosphate can be easily distinguished from FDP, using high performance liquid chromatography (HPLC).

This technical factor also strongly supports the assertion that partial lyophilization of FDP, which leaves in a water content higher than 10% to give a stable preparation, would not be obvious to anyone with ordinary skill in the art. Since hydrolysis of the phosphate bonds of FDP is the crucial problem that must be overcome to provide a preparation with adequate chemical stability, then anyone with ordinary skill in lyophilization chemistry would normally assume that the water content must be reduced as low as possible, even if extreme measures are required, to reduce the risk of hydrolysis. The result discovered by the Inventor herein pointed in the exact opposite direction from what was expected.

As noted above, the 1-month stability test period is merely a benchmark standard, for analytical and comparative purposes. Many of the FDP preparations disclosed herein have aged for a year or more and still satisfy the impurity standards by a comfortable margin. Samples that were analyzed shortly before this application was filed showed less than 1% total impurities after 425 days of storage at room temperature.

It should also be noted that samples of the Biochemica Foscama lyophilized preparation have been analyzed, by the Applicant, for purity, using HPLC analysis (which detects hydrolysis, but is less likely to reliably detect caramelization). The samples tested contained more than 1% of single impurities, and therefore did not meet the FDA standard which was applied to the Applicant herein.

Accordingly, one object of this invention is to disclose a method of partially lyophilizing FDP, to create a sterile sealed product that contains at least 10% and up to about 25% residual water content, by weight.

Another object of this invention is to disclose that partially lyophilized FDP which contains 10% to 25% residual water, by weight, is chemically stable and has good shelf life when stored for months at room temperature without refrigeration.

Another object of this invention is to disclose that secondary vaporizing agents, such as tertiary butyl alcohol, can be used during the lyophilization of FDP to provide improved final products.

Another object of this invention is to disclose that partially lyophilized FDP offers a stable preparation that enables emergency injection of FDP into patients or victims who are suffering medical crises (such as a heart attack, suffocation, loss of blood due to injury, etc.) and who need immediate medical assistance. Such treatment can be administered by any person (such as an ambulance attendant, policeman, or nursing home attendant) who is trained to administer an intravenous injection, without requiring any delays while waiting for transportation or access to a doctor or diagnostic equipment.

Another object of this invention is to disclose prepackaged injection kits for use in medical emergencies. These injection kits contain partially lyophilized FDP, as disclosed herein, along with a sterile aqueous solution, to reconstitute the FDP into an injectable liquid, and a syringe and needle. Preferably, all of these components should be contained within a durable case, made of a material such as hard molded plastic. This would render such emergency injection kits suitable for being carried and kept in places where they can facilitate rapid emergency use, such as in ambulances, trunks of police cars or firetrucks, and first aid kits in nursing homes and at swimming pools and beaches.

These and other objects of the invention will become more apparent through the following summary, drawings, and description of the preferred embodiments.

SUMMARY OF THE INVENTION

A practical and economic method is disclosed for preparing a partially lyophilized (freeze-dried) powder or solidified cake containing fructose-1,6-diphosphate (FDP), a naturally-occurring chemical which is an intermediate in glycolysis. The preferred methods leave at least 10%, and up to about 25%, residual water (by weight) in the powder or cake. This surprisingly high moisture content does not degrade or limit FDP's stability or shelf life, and it provides for faster, less expensive processing. The methods disclosed herein also allow direct lyophilization inside a vial or other sealed container that will hold the lyophilized FDP during storage, shipping and handling. This avoids any need for milling, handling, or other treatment under conditions that might endanger its sterility. Among other benefits, this invention provides for emergency injection kits containing lyophilized FDP, sterile aqueous solutions, and syringes, that can be carried in ambulances, police cars, etc. These emergency kits will allow rapid injection of FDP into victims of medical emergencies such as heart attacks, severe blood loss, suffocation, etc.

DESCRIPTION OF THE PREFERRED EMBODIMENTS

Figure 1:
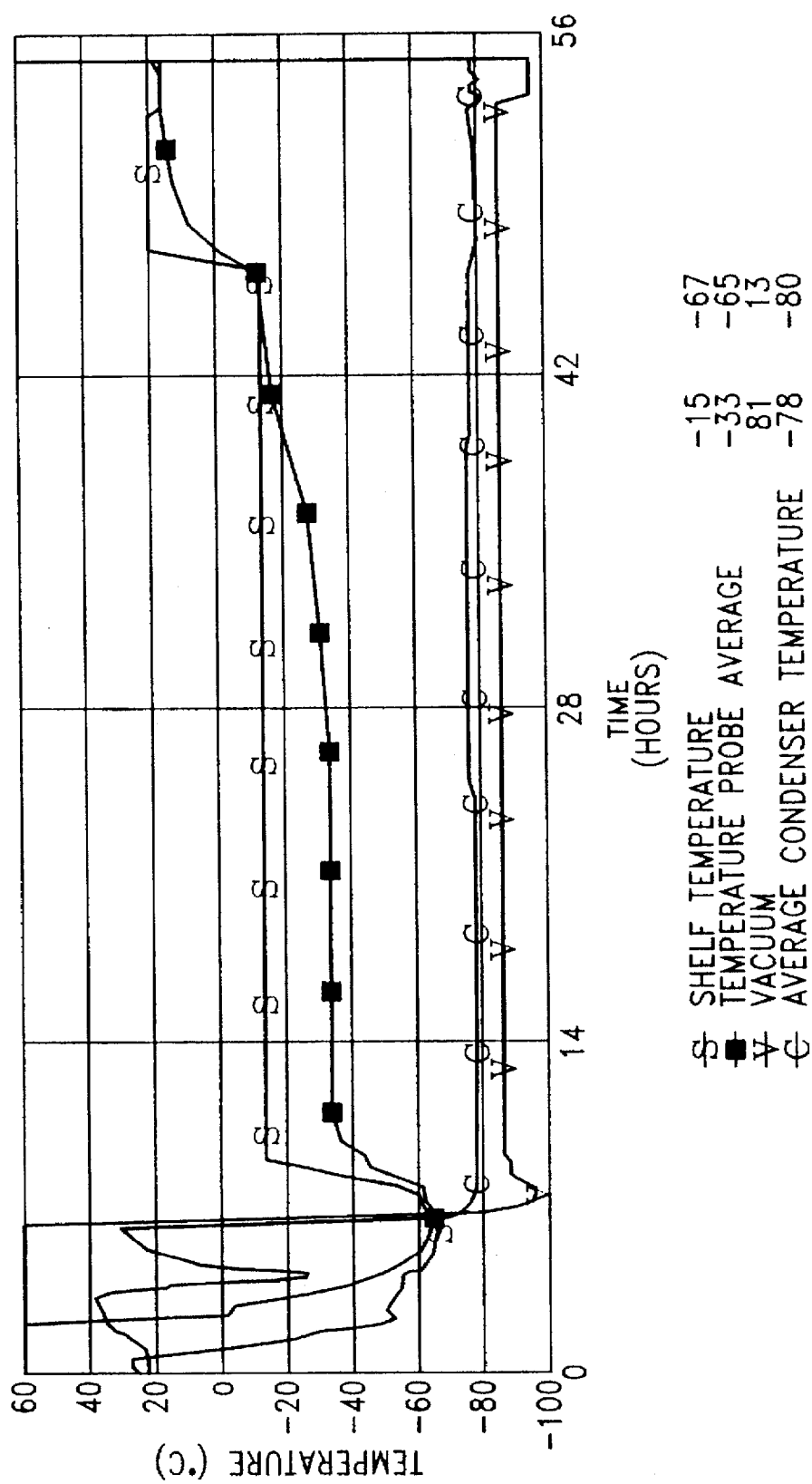
FIG. 1 is a graph showing temperatures, as a function of time, for a preferred partial lyophilization procedure for FDP as described herein.

A method is disclosed herein for preparing a partially lyophilized (freeze-dried) powder or solidified cake containing fructose-1,6-diphosphate (FDP), in a powder or cake form that contains residual water in a range of at least 10% and up to about 25%, by weight. This is less than the 26.18% water that is contained in conventional FDP octahydrate crystals, but it is substantially more water than is contained in most conventional forms of fully lyophilized drugs, which usually contain less than 2% residual water. By allowing these high levels of residual water to remain in the partially lyophilized FDP preparations disclosed herein, the energy, equipment, and time requirements for processing are greatly reduced, and the process is rendered practical and economical. However, the partially lyophilized FDP products disclosed herein do not suffer from reduced quality, stability, or sterility.

The method disclosed herein produces solidified FDP preparations that are "stable" for at least one month when stored at 25° C. in a sealed vial. Terms such as "stable" and "stability" refer to lyophilized preparations that meet or surpass the FDA-endorsed purity requirements for human use (i.e., 5% or less total impurities, and 1% or less of any single impurity, by weight). The post-storage test period referred to in the claims (one month) is merely a benchmark standard, for convenient and objective analytical and comparative purposes. Many of the FDP preparations disclosed herein have aged for a full year or more, and still surpass the FDA's purity requirements by a comfortable margin.

To be covered by the claims, a "stable" FDP preparation must also remain in good, uniform condition when visually inspected through the glass walls of a vial. It must not suffer obvious levels of caramelization or formation of enlarged or agglomerated particles that are clearly different from the remainder of the lyophilized FDP.

A preferred embodiment of this method of lyophilizing FDP comprises the following steps:

(1) Creating a aqueous solution of FDP, preferably containing FDP in a range of about 10% to about 40% FDP, by weight;

(2) Mixing the aqueous solution of FDP with a second agent which crystalizes at the temperatures of interest and which subsequently sublimates (vaporizes into gas) readily and rapidly at temperatures slightly below the "glass transition temperature" of FDP, which is about −33° C. Due to these physical traits, the second agent creates porosity and permeability in the frozen solid, thereby decreasing the amount of time required for the frozen water to leave the solid during lyophilization, and producing a better final product. One such second agent is tertiary-butyl alcohol, also called t-butanol. Various other agents, such as ethanol, isopropanol, and other organic solvents, have been used in similar ways. Although none of these have been identified, in the research performed to date, which perform as well as tertiary-butyl alcohol in the temperature and vacuum ranges that are suitable for FDP, such other agents may be suitable for use as described herein, if proper vacuum and temperature combinations are developed and optimized for any such candidate agent.

(3) Loading a predetermined quantity of the sterile mixture into a vial or other small container which is intended to hold the FDP in sterile lyophilized form during storage, shipping, and handling;

(4) Placing the vial and mixture in a lyophilization chamber which can generate and sustain suitable combinations of freezing temperatures and vacuums;

(5) Reducing the temperature of the solution to below the glass transition temperature of FDP, to freeze the mixture;

(6) Subjecting the frozen solid mixture to a primary drying step, in which a predetermined vacuum is sustained for a sufficient time to remove both (a) a majority of the water which is present as ice, and (b) the second agent.

(7) Subjecting the remaining frozen material to a second drying step, which removes some but not all of the so-called "bound" water (water of hydration).

If done properly, these steps will leave behind a powdered or caked residue which contains lyophilized FDP in a high-quality, easily-dissolved form which has good shelf-life, and which also has a residual water content of at least 10%, up to about 25%, by weight.

As used herein, the term "solidified" is used to refer to powdered, granulated, caked, or other comparable non-liquid forms of FDP which contain less than 25% residual water. For purposes of stability and handling, the important distinction is between liquid mixtures (which are inherently unstable, due to hydrolysis of FDP) and solidified forms, which are stable if prepared properly as described herein. Distinctions between powdered, granulated, or caked forms of FDP are relatively insignificant for the medical uses described herein, since even relatively hard cakes will dissolve fairly rapidly, once water or another suitable liquid has been added to reconstitute FDP into an injectable liquid.

The FDP preparations disclosed herein, having between 10 and 25% residual water, are referred to interchangeably in the text of this application as either "partially lyophilized" or "lyophilized". They are lyophilized, since they have indeed been subjected to a lyophilization process. However, they must be recognized as being only partially lyophilized, when measured by conventional lyophilization standards for pharmaceutical products; several examples of the conventional pharmaceutical standards are cited and quoted in the Background section.

Figure 2:
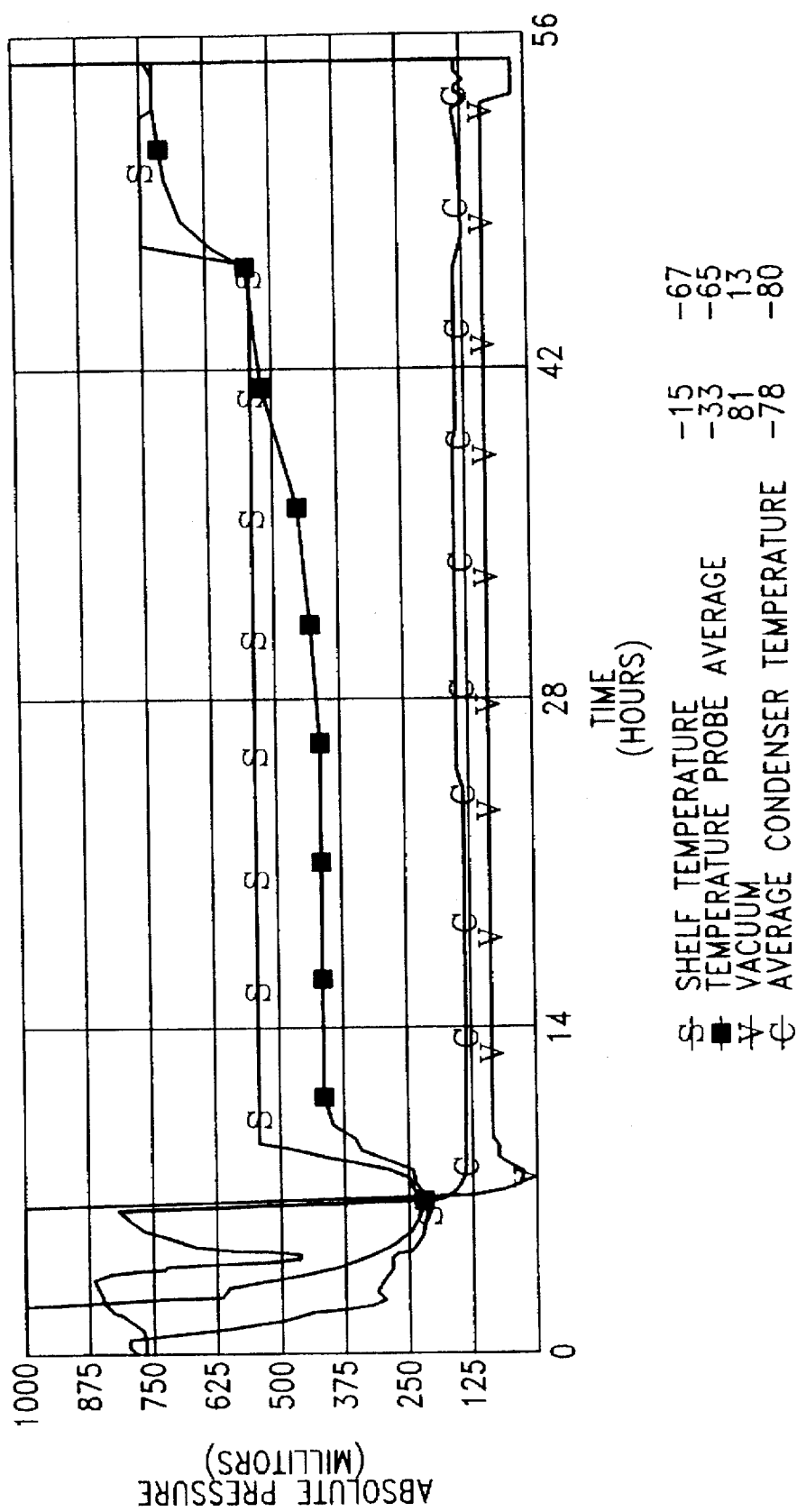
FIG. 2 is a graph showing vacuum pressures, as a function of time, for a preferred FDP partial lyophilization procedure as described herein.

FIGS. 1 and 2 provide temperature and pressure profiles, shown as a function of time (in hours), for carrying out a preferred partial lyophilization process as described herein. As shown in those figures, this process can be completed in about 2 to 3 days, which is much faster than would be required if full lyophilization were carried out to take the residual water content down to 2% or less.

The exact durations, temperatures, and vacuum levels shown in FIGS. 1 and 2 are not critical and can be varied if desired, provided that the final lyophilized product meets the relevant quality and stability requirements. For example, if more time is allowed in any particular stage of processing, that stage can be carried out at a lower temperature. However, requirements of more time and lower temperatures both translate into greater expense. Similarly, higher vacuum levels can accelerate the drying process, but may also create other problems, such as splattering, loss of FDP from a vial, and creation of uneven particle sizes and other inhomogeneities in the final product, and therefore need to be optimized to avoid such problems. Accordingly, the goal is to use the fastest, warmest profile that will consistently and reliably create a stable, uniform, high-quality FDP preparation with a long shelf life.

Another major advantage of the method described herein should also be noted. The lyophilization process disclosed herein can be carried out after loading a FDP-containing liquid mixture into vials that will serve as the final sealed and sterile containers for the FDP powder or cake. This eliminates any need for grinding, milling, or other handling or preparative steps that would be required if the powder or cake were to be prepared in bulk (presumably in a large shallow tray) and then ground or milled into particulates (or otherwise processed) before being loaded into a small vial. Such processing steps would require very expensive machinery, as well as elaborate and tedious procedures to ensure that sterility is not jeopardized. In-package lyophilization, to remove the water from a liquid mixture that has been loaded into a vial that will serve as its final sealed container, is strongly preferable, and it is enabled in a practical and economic manner by the method disclosed herein.

One of the major benefits of this method is that it substantially reduces costs, and allows for practical and economic commercialization and widespread distribution and sale of partially lyophilized injectable FDP, in a safe and sterile form which is stable for months at room temperature. Lyophilization of other injectable drugs is well known, and methods are taught in the prior art which could, if desired, be directly adapted to creating fully lyophilized FDP, containing a conventional percentage of water as present in most lyophilized drugs (usually about 2% or less, by weight). However, the invention herein is partially based on the discovery that a substantially higher quantity of water can be left in the final powder or cake, without degrading or jeopardizing the stability, safety, or potency of the partially lyophilized FDP, which contains an abnormally high quantity of water (greater than 10%).

This invention is also based on the realization that FDP can, and should, be injected into someone suffering from a medical crisis involving ischemia, hypoxia, or loss of blood (such as a heart attack, shooting, stabbing) as soon as possible after the crisis begins, without waiting for a full diagnosis of the victim's condition by a physician. If injected as quickly as possible after a serious accident or medical crisis, FDP may be able to provide extremely important medical benefits to a patient or victim, and it will not generate any significant risks or cause any adverse side effects in people who do not need it.

This type of emergency pre-diagnostic use, and the various medical indications that warrant such treatment, are described in more detail in co-pending U.S. patent application Ser. No. 08/646,600, filed in May 1996, also assigned to the Applicant herein (Cypros Pharmaceutical Corporation). The contents of that application are incorporated herein by reference.

Figure 3:
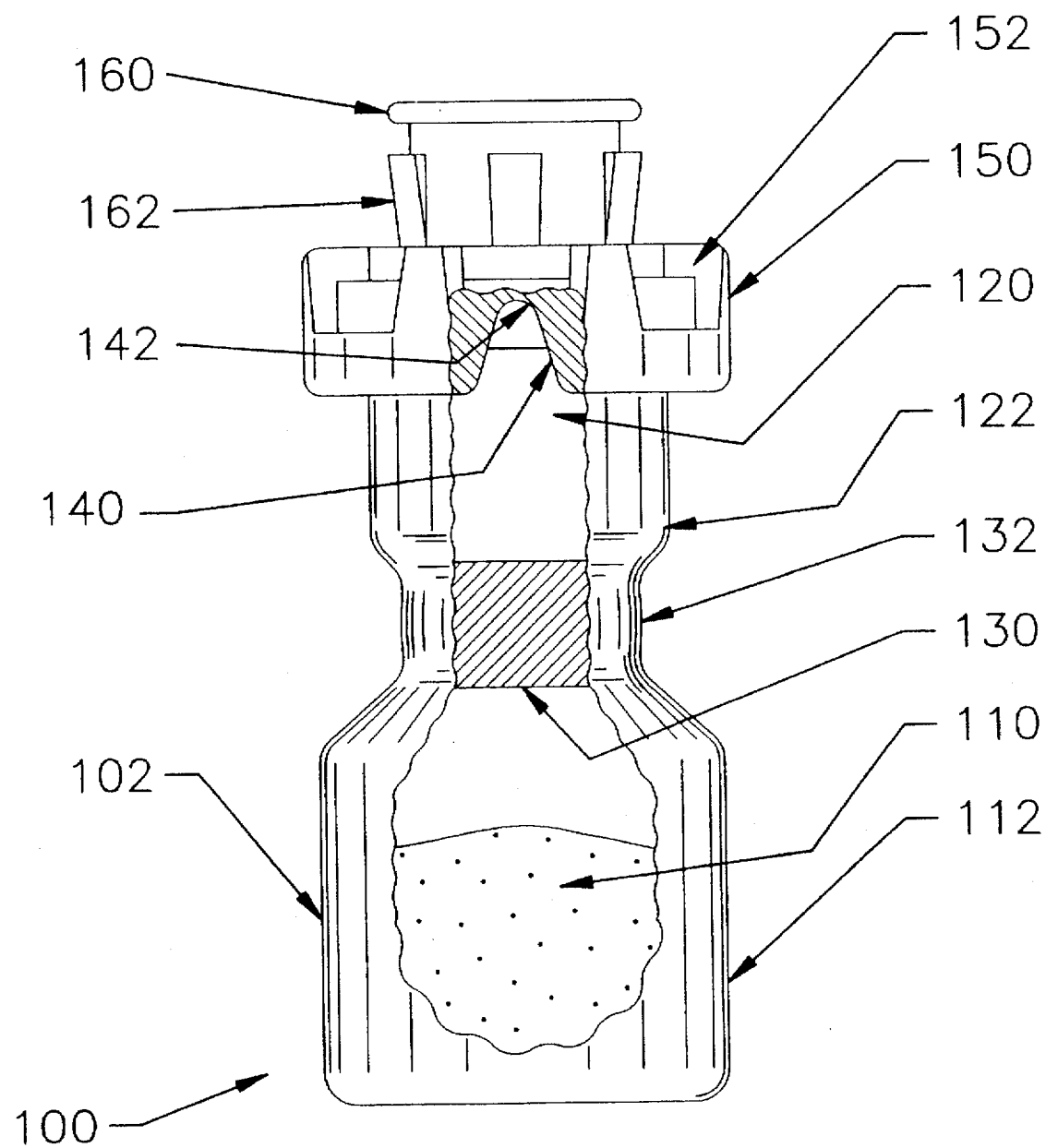
FIG. 3 is a cutaway side view of a dual-compartment sealed sterile vial containing a partially lyophilized FDP powder or cake in one compartment, and a sterile aqueous solution in a second compartment. The septum that separates the two compartments can be pushed out of its sealed blocking position, to reconstitute an aqueous solution of FDP for injection into a human patient.

Accordingly, an emergency injection kit, which contains all items necessary for rapid reconstitution and injection of lyophilized FDP, is also disclosed herein, as part of this invention. A conventional two-chamber vial assembly 100 is shown in FIG. 3; this type of vial device is shown in various U.S. patents, including U.S. Pat. No. 4,781,354 (Potts 1981). This vial assembly comprises an outer wall 102 which is roughly cylindrical with a flat bottom, and which defines and encloses a lower chamber 112 (which must be filled first, during the manufacturing process) and an upper chamber 122, separated from each other by a narrower constriction band 132.

This vial structure is conventional and well-known, and the point of novelty of the vial shown in FIG. 3 is that it contains a partially lyophilized FDP powder or cake 110, as disclosed herein, in lower chamber 112. The vial also contains sterile water 120 (preferably in a solution intended for injection that also contains other conventional ingredients such as dextrose, Ringer's lactate, etc.), in upper chamber 122.

The two chambers 112 and 122 are separated from each other by a water-tight partition or "septum" 130, which is a non-permeable disk made of an inert flexible material such as butyl or silicone rubber, which has been force-fitted into the constriction band 132, which holds septum 130 in place until the FDP is needed.

A second non-rigid plug 140, usually made of butyl rubber, is mounted in the neck of the vial, and is secured to the vial by means of a metallic cap 150. This soft, flexible plug 140 allows a sharp tip of a hypodermic or tubing needle to be inserted into upper chamber 122, through a relatively thin upper wall portion 142 of the plug 140. This allows removal of a reconstituted liquid from the vial, so that the liquid can be loaded into a hypodermic syringe or infusion bag, for injection into a patient.

The metallic cap 150 interacts with plunger 160, allowing the plunger to be forced down, through an orifice which occupies the center of the cap 150. Outward-extending locking ears 162 in the sides of plunger 160 interact with accommodating slots 152 in the metallic cap, to lock the plunger in position once it has been pushed down into the cap.

When an emergency arises and the FDP is needed for injection into a patient, plunger 160 is depressed. This pushes septum 130 out of position in the constriction band 132, aided by two factors: (a) the inert gas (usually nitrogen or argon) that fills the top of chamber 112 is compressible and allows downward motion of the septum 130 under pressure; and (2) the aqueous liquid which fills the upper chamber is non-compressible, and causes the full force placed on plunger 160 to be pressed against the movable septum 130.

As soon as the septum 130 falls into the lower chamber 112, the dry FDP 110 comes into contact with the aqueous solution 120, and the two are mixed together thoroughly, by shaking the vial. The septum can bounce around inside the lower chamber 112 during this shaking process, and acts as a mechanical agitator to promote full mixing, and to help rapidly break apart the cake, if the dry FDP 110 was in a solidified cake rather than a powder.

The term "vial" is used broadly herein, to refer to any drug-packaging device that is designed and suitable for sealed and sterile storage, shipping, and handling of small (e.g., single-dosage) quantities of drugs. The two-chamber vial shown in FIG. 3 is only one example of the various types of two-chamber vials that are known in the art. Single-chamber vials are also well known; for example, a single-chamber vial designed for use with intravenous infusion bags (which are carried by any ambulance, and which can enable injection of much larger quantities of liquid drugs than conventional syringes) is illustrated in U.S. Pat. No. 4,871,354.

Figure 4:
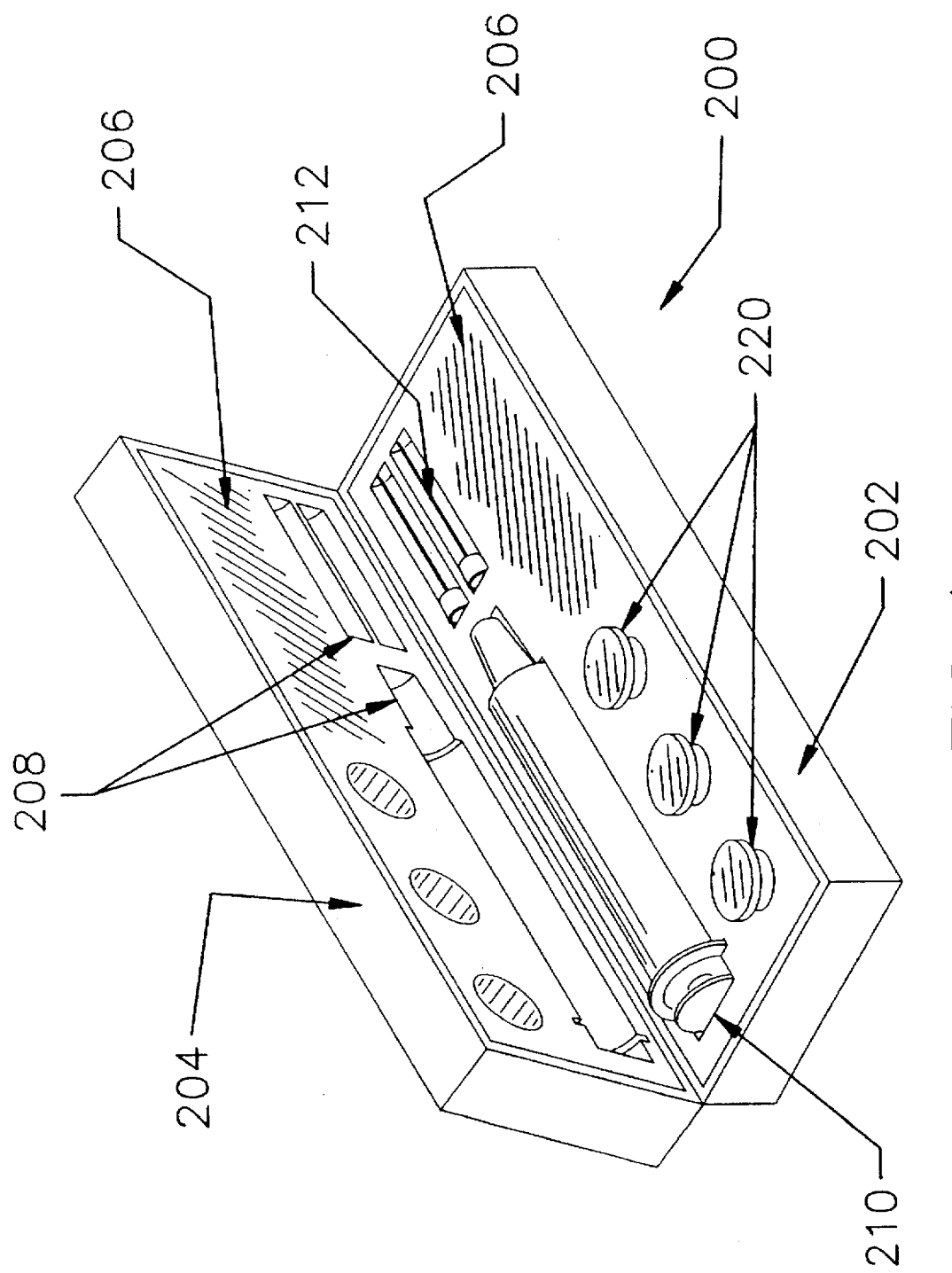
FIG. 4 is a perspective view of a hard-shell plastic case which encloses and protects a hypodermic syringe and needle, several sealed vials containing partially lyophilized FDP, and a sealed container of an aqueous solution (such as a dextrose solution, Ringer's lactate, etc.) for reconstituting the FDP into aqueous solution. This injection kit is designed for emergency use, so that someone who is not a physician but who is trained to deliver injections (such as ambulance attendants, police, military personnel, nursing home attendants, etc.) can help people suffering from crises such as heart attacks, shootings, stabbings, auto accident, etc.

One or more vials 100 (either two-chambered vials as shown, for use in police cars, firetrucks, etc., or single-chamber vials for use with infusion bags in ambulances, nursing homes, etc.) can be included in an emergency injection kit 200, shown in FIG. 4. This kit 200 is enclosed in a durable hard-shell case having a bottom portion 202 and a hinge-attached top portion 204, made of a molded material such as a hard plastic. The external shell can also enclose padding material 206, made of, for example, a lightweight, highly porous foam rubber which has been machined to provide shaped cutaway pockets 208 which will securely hold syringe 210, hypodermic needles 212 (preferably, at least two needles should be provided, in case one gets damaged), and vials 220 containing lyophilized FDP (as many vials as desired can be provided, each vial containing a standard quantity of FDP, such as 5 grams). This will allow the case and padding material to protect the fragile contents without being damaged, even if subjected to fairly rough treatment, as might occur, for example, in the trunk of a police car. The syringe and needle can be carried in separated cutaway holders inside the hard-shell case. The syringe can be sealed inside a sterile plastic wrapper (not shown), and each needle can be carried inside a small rigid plastic shell (not shown), to protect it and prevent it from jabbing anything.

The inclusion of lyophilized FDP in this type of emergency injection kit can allow immediate on-site treatment of a patient or victim of a severe medical crisis (such as a heart attack, shooting or stabbing, or auto accident) by anyone who can administer an intravenous injection. This may include, for example, ambulance attendants, police, firemen, nurses, nursing home attendants, emergency room attendants, lifeguards, and relatives of people who suffer from various diseases, such as heart disease or sickle cell anemia.

Accordingly, the emergency injection kit 200 does not require refrigeration, and it is designed to withstand the type of rough treatment that might occur if carried in ambulances, police cars, firetrucks, etc., or if stored in first aid cabinets, boxes, or closets, at locations such as nursing homes, lifeguard stations, and in the homes of people suffering from various diseases, such as heart disease or sickle cell anemia.

When FDP is administered as quickly as possible to a patient suffering an ischemic or hypoxic crisis, it can substantially reduce cell death and tissue damage, especially in the heart. However, if FDP is mistakenly administered to someone who does not need it and cannot benefit from it, it will not create any known significant adverse effects or pose any known significant risks.

Accordingly, injection of FDP should not be delayed until a patient can be transported to a doctor or hospital for complete diagnosis and treatment; instead, for maximal effectiveness, injection should occur as soon as possible after an accident or after a patient began to display symptoms of a medical emergency, such as a heart attack.

FDP's combination of valuable traits—protective efficacy in people who need it, combined with very low risk in people who don't need it—render it well-suited for pre-diagnostic use in medical emergencies, using injections that can be administered long before a patient arrives at a hospital for full treatment by a physician. As is well known to physicians, the speed with which proper care is initiated often makes an critical difference in survival rates, in the amount of permanent damage suffered by a patient or victim, and in the personal, family, and social costs that arise after a major medical emergency. This type of emergency pre-diagnostic treatment has never been available before, and it is enabled, for the first time, by the lyophilized form of FDP disclosed herein.

However, emergency use is not the only valid use for lyophilized FDP as disclosed herein. Other medical uses of FDP are also rendered substantially more convenient by this partially-lyophilized preparation. It has recently been shown, in human clinical trials designed and funded by the same assignee herein (Cypros Pharmaceutical Corporation), that if FDP is intravenously infused into a patient who is preparing to undergo coronary artery bypass grafting (CABG) surgery, during roughly a half-hour period before the surgery begins, then the stress and damage which are inflicted on the heart during the surgery will be significantly reduced.

A sterile, stable lyophilized FDP preparation as disclosed herein can facilitate such medical uses, for at least two reasons. First, hydrated forms of FDP generally require refrigeration, even if stored in completely sterile form with no bacteria in them, in order to minimize hydrolysis or other chemical degradation, which is a problem whenever mixtures of FDP dissolved in water must be stored for prolonged periods. Even in settings which have refrigerators, such as hospitals and clinics, refrigeration is a troublesome and expensive storage method. Using lyophilization to eliminate the need for refrigeration (or, for greatly reducing the volumes of any FDP containers that are stored in a refrigerator) provides substantial benefits. And second, hydrated forms of FDP will eventually hydrolyze, even if refrigerated, largely because the two phosphate bonds in FDP are highly vulnerable to hydrolysis (as noted above, the vulnerability of these two bonds to hydrolysis is one of the reasons that the stability of a partially lyophilized FDP product with 10% or more residual water was quite surprising). Minimizing such unwanted chemical degradation, by avoiding aqueous mixtures until immediately before injection, is an important benefit of lyophilization.

At least some the potential medical uses for FDP will be enhanced if an FDP-containing liquid can be infused into a patient using intravenous infusion bags, which contain much larger quantities of liquid than a syringe. Accordingly, lyophilized FDP as described herein can be created and stored in a single-chamber vial or other container designed for use with an intravenous infusion bag. Such infusion can be performed in a hospital, clinic, ambulance, nursing home, etc.

Two-Chamber Vials

A variety of drug containers are known in the art, which contain two chambers that are separated from each other in a water-tight manner by a septum. One such device, described in U.S. Pat. No. 4,258,845, is sold under the trademark, "Act-O-Vial" by the Upjohn Company (Kalamazoo, Mich.). Other U.S. patents which also describe other two-chamber devices for drugs include U.S. Pat. Nos. 5,385,546; 5,350,372; 5,336,180; 5,335,773; 4,871,354; and, 4,258,845. There are also several other systems in commercial use, whose patent status is not currently known by the Applicant. These include the "UNIVIAL" system and the "ADD-Vantage" systems, sold by Abbott Laboratories, and the "PIGGYBACK" vial sold by SmithKline Beecham.

Nearly any of these devices are suitable for storing a partially lyophilized FDP powder or cake in one chamber, and water in the other chamber.

Another device worth noting is sold under the trademark, "SMART DOSE" by IVAC Medical Systems, San Diego, Calif. It is described in U.S. Pat. Nos. 5,398,850 and 5,398,851. Instead of being a self-contained two-chamber device, it is an infusion bag and pump combination which contains a sterile dextrose, Ringer's, or saline solution, and which is designed to be used easily with lyophilized drugs. FDP can be partially lyophilized as disclosed herein, in standard vials (such as the 100 mL vials used in the Examples), and then used in conjunction with the "SMART DOSE" system. This system may provide a highly practical way of administering FDP in certain settings, such as in ambulances.

Formulations and Dosages

Preferred dosages for emergency bolus injection from a syringe will generally be in the range of about 50 to about 400 mg/kg (i.e., milligrams of FDP per kilogram of patient body weight). Since most adults weigh between 50 and 100 kg (110 to 220 lb), an emergency injection kit which contains vials holding about 15 grams of FDP can provide dosages in the desired range, with a value of about 300 mg/kg for an adult weighing 50 kg (110 pounds), and about 150 mg/kg for an adult weighing 100 kg (220 pounds).

All of the vials described in the Examples contain 5 grams of FDP in 100 mL molded glass vials. This was used as a standardized quantity during the research described herein. Although it is possible to increase the quantity of FDP in each vial, it is likely that economic and technical factors may lead in the opposite direction (i.e., to smaller quantities of FDP in each vial), for several reasons. First, since vials are arranged in offset rows (in a classical honeycomb pattern) on a shelf in a lyophilization chamber, vials with small diameters make better use of the shelf space inside a chamber, than vials with large diameters. Smaller vials can be packed together more closely, fill up the horizontal area of a shelf better, and leave less empty between the vials. Second, a relatively shallow liquid in a vial takes less time to lyophilize than a deeper liquid; glass vials are cheap, while chamber time is expensive. And third, vials formed from glass tubing have more consistency in the thickness of their walls and bottoms, than vials formed by molding. This wall uniformity factor reduces potential problems of temperature differentials and product inconsistencies, in products that are lyophilized in vials made from glass tubing. However, tubing vials are usually limited to about 50 mL or less in volume; vials holding 100 mL or more usually need to be made from molded glass.

All of these economic factors point toward smaller vials with smaller quantities of lyophilized FDP. However, preparations containing 5 grams each in molded glass vials have been made with consistently good product quality, in the lab-scale tests described herein, and these results will be evaluated during production scale-up, to determine whether vials holding 5 grams/vial (or possibly even more) can be mass-manufactured without losing product quality.

Regardless of vial size or weight, glass vials are cheap, compared to the products they contain, and as many vials as desired can be included in any hard-shell injection kit as described herein. The injection kit shown in FIG. 4 shows four vials with 5 grams of FDP in each, for a total of 20 grams of FDP in the kit.

Any suitable (i.e., pharmacologically acceptable) salt of FDP can be used, such as a sodium salt, or divalent salts such as calcium or magnesium salts, or mixtures thereof. In general, potassium salts should not be administered intravenously, since an abrupt infusion might interfere with cardiac functioning and certain other cellular functions. The sodium salt is used most commonly, and was used to develop the processing steps described herein and shown in FIGS. 1 and 2. In the quantities that are relevant herein, the amount of sodium contained in this salt will not have any adverse effects on the vast majority of people who are likely to need it. In hospital settings, if sodium causes serious concern in a specific patient, the patient can be treated with a diuretic drug to increase the elimination of sodium in urine or feces.

It is recognized by the Applicant that other salts are likely to behave differently from the sodium salt, which crystallizes as an octahydrate. Accordingly, other salts (such as calcium, barium, or cyclohexylammonium salts) will also be evaluated for possible use as described herein.

Isomers other than fructose-1,6-diphosphate cannot be used. Although certain other isomers (including fructose-2,6-diphosphate) occur naturally in cells, they serve other purposes and are not created or consumed as intermediates in the glycolysis pathway.

It is currently believed that nearly any conventional injection liquid (such as a dextrose solution, Ringer's lactate solution, and normal saline solution) can be used as a liquid for reconstituting the lyophilized FDP preparations described herein. Distilled and de-ionized water may even be suitable, since the FDP will normally be in a sodium or other salt form, and can provide sufficient salt to avoid or minimize osmotic disruption after injection.

EXAMPLES

EXAMPLE 1

ABILITY OF FDP TO BOOST INTRACELLULAR ATP LEVELS

In order to be effective in boosting glycolysis and generating ATP, exogenous FDP must be able to permeate or be transported into cell interiors, because that is where glycolysis occurs. Since FDP, with its two phosphate groups, carries a strong negative charge, it is widely presumed to suffer from low permeation rates into cells. A large part of the general skepticism among doctors about the cytoprotective capabilities of FDP apparently centers on this presumed limitation.

To evaluate this factor, human astrocytoma cells which had been grown to confluence were incubated for 1 hour with 1 micromolar of tritium-labelled ($^3$H) adenosine (purchased from Morovek Biochemicals, Inc., Brea, Calif.). Any radiolabelled adenosine which remained in the extra-cellular culture medium was washed out after 1 hour.

The cells were then divided into 2 aliquots. One aliquot was incubated for 6 hours with 3.5 mM FDP, while the other aliquot (containing the control population of cells) was incubated identically, but with no FDP. This allowed cells from a single, identically-treated, same-day population to be used as control cells. This approach was used because when a population of cells is supplied with radio-labelled adenosine, it will generate substantially different radiolabelled ATP readings on different days, depending on various factors such as (1) the status and activity levels of the cells on a specific day, (2) variances between labelling intensity in different batches of radiolabelled reagents, and (3) variances in calibration and settings of the analytical equipment. Because of these differences, count-per-minute data tend to be highly variable between different days, while percentage increases are much more consistent and reliable if a single batch of cells is divided into control and treatment aliquots and then treated and tested on a single day using the same reagents and equipment for both aliquots.

After a 6-hour incubation with or without FDP, both aliquots of cells were killed and extracted with 0.4M perchloric acid and neutralized with an alanine-freon mixture. ATP concentrations were analyzed using polyethylene imine-cellulose thin layer chromatography. Radioactivity was analyzed in a Beckman liquid scintillation counter.

The results, in Table 1, showed that under normoxic conditions, the addition of FDP to the extra-cellular liquid roughly doubled the quantity of radiolabelled adenosine converted into ATP; treated cell values averaged 198.7 percent of untreated cell values, with a standard deviation of 17%. Under anaerobic conditions, the boosting effect of extra-cellular

TABLE 1

EFFECT OF FDP ON INTRACELLULAR ATP LEVELS IN CULTURED ASTROCYTES

| Experiment # | FDP (mM) | [ATP]CPM/Plate | % Increase in ATP After FDP |
|---|---|---|---|
| 1 | 0 | 121,800 | 82% |
|   | 3.5 | 220,700 |  |
| 2 | 0 | 110,600 | 93% |
|   | 3.5 | 211,900 |  |
| 3 | 0 | 59,000 | 142% |
|   | 3.5 | 143,700 |  |
| 4 | 0 | 119,000 | 54% |
|   | 3.5 | 183,500 |  |
| 5 | 0 | 104,300 | 178% |
|   | 3.5 | 288,800 |  |

Note: All values are the average of two plates.

FDP on intracellular ATP was even stronger; treated cell values were 243±30%. Since the conversion of adenosine to ATP only occurs inside cells, this provides direct evidence that FDP enters mammalian cells in sufficient quantities to substantially increase ATP levels inside the cells.

EXAMPLE 2

SAFETY OF FDP IN COMPROMISED PATIENT POPULATIONS

Tests were carried out to evaluate the benefits of FDP in reducing ischemic heart damage in patients who were undergoing circulatory bypass of the heart during coronary artery bypass grafting (CABG) surgery. In these tests, coronary bypass patients were pre-treated with an intravenous infusion of FDP at a dosage of 250 mg of FDP per kilogram of patient body weight, beginning about 10 to 30 minutes before circulatory bypass began. This gave the FDP sufficient time to permeate into the heart tissue before it was subjected to ischemic conditions under cardioplegia.

Figure 5:
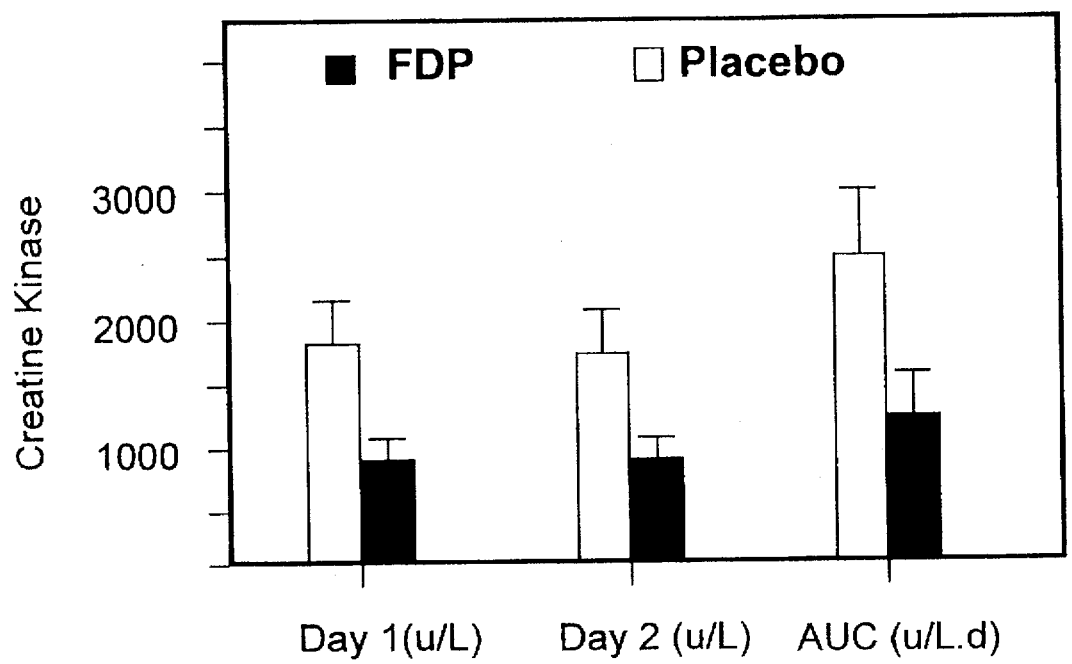
FIG. 5 shows that infusion of FDP prior to bypass surgery caused a statistically significant reduction in CK levels in circulating blood plasma (measured on the first and second post-operative days) compared to a placebo treatment.
Figure 6:
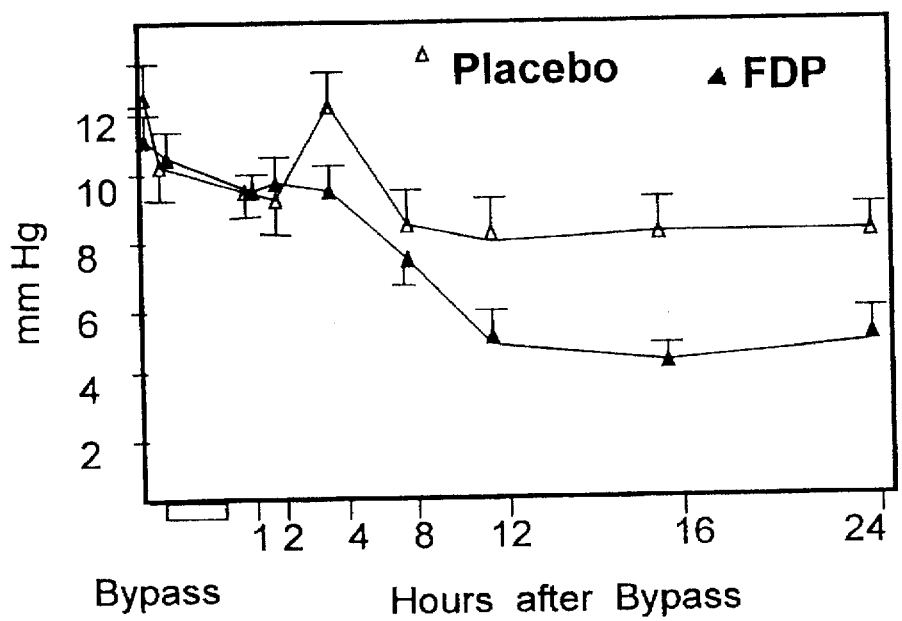
FIG. 6 shows that infusion of FDP prior to bypass surgery helped patients regain a more normal left-side heart function, as measured by reduced elevations of pulmonary artery wedge pressure on the first post-operative day. The benefits were statistically significant.
Figure 7:
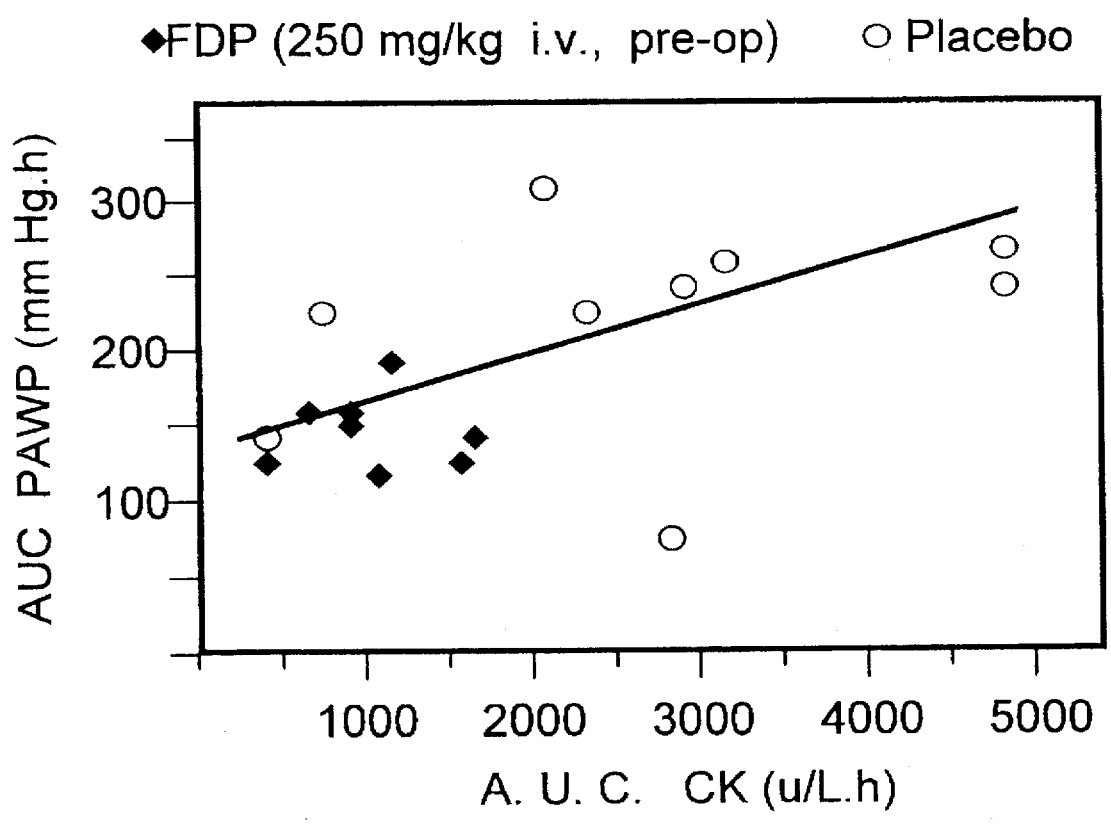
FIG. 7 is a graph which shows how the biochemical benefits of FDP (measured by CK levels in blood plasma), correlate with the mechanical and hemodynamic benefits of FDP (measured by reduced abnormalities in pressure values). This correlation is statistically significant, and it confirms that FDP provided both biochemical and hemodynamic benefits.

As indicated in FIGS. 5–7, pre-bypass injection of FDP significantly reduced the level of ischemic damage that was inflicted on treated patients, compared to control populations that did not receive any FDP, as measured by both biochemical and mechanical means. On a biochemical level, FDP significantly reduced the amount of an enzyme called creatine kinase (CK) which was released into blood by cells, as shown in FIG. 5. Since CK is a very large intracellular protein that cannot be transported across intact cell membranes, this enzyme is commonly used as an indicator of the extent of heart cell death and permanent tissue damage in cardiac patients.

On a mechanical level, pre-bypass treatment with FDP also substantially reduced a hemodynamic abnormality which involves an increase in "pulmonary artery wedge pressure" (PAWP), as shown in FIG. 6. An increase in PAWP values indicates that a patient's heart has suffered some sort of damage or is struggling with some form of abnormal stress. Nearly all cardiac surgery patients undergo an increase in PAWP values in the hours or days after surgery. If a drug can reduce the undesired increases in PAWP values, it indicates that the drug apparently helped reduce the severity of the stress that was imposed on the heart by the surgery.

As shown in FIG. 7, there was a correlation between the biochemical and hemodynamic/mechanical benefits of pre-bypass treatment using FDP. The ability of FDP to reduce the indicators of stress and damage in the heart, using two independent measurements, confirm that FDP can truly benefit the heart and reduce heart stress and damage during circulatory bypass when the heart muscle must undergo a period of ischemia.

These tests were carried out on 20 patients, under the supervision of a qualified cardiac anesthesiologist. These tests were initiated and sponsored by Cypros Pharmaceutical Corporation (the assignee and applicant herein), which obtained approval from the United States Food and Drug Administration prior to carrying out these Phase II human clinical trials. Phase I trial requirements (to establish baseline values for FDP using tests on healthy volunteers) were waived by the F.D.A., since FDP is a naturally occurring biochemical that occurs only as a short-lived intermediate which is quickly consumed during glycolysis.

These tests were carried out using placebo-controlled, double-blind randomized design, and were performed in accordance with all FDA guidelines for Good Clinical Practice (GCP) and the Declaration of Helsinki principles. To the best of the Applicant's knowledge and belief, this was the first such clinical trial ever conducted which tested FDP as a protective agent in this manner or for this use, and there is no other comparable agent being used for this purpose anywhere in the world.

During these tests, there was no indication whatsoever of any adverse effects of FDP on any of the patients, even though all of the patients who were tested were medically compromised and in poor health. A number had already suffered heart attacks, and all were suffering from coronary artery occlusions that were severe enough to require open-chest surgery, rather than balloon angioplasty, drug treatment, or other less-invasive procedures.

Furthermore, since FDP is a short-lived intermediate which is quickly consumed by glycolysis, there is every reason to believe that FDP poses no significant risks, or only very low and minimal risks of any significant adverse effects, in patients who may not need it.

To the best of the Applicant's knowledge and belief, these are the first clinical data ever reported on FDP which were gathered in tests that were carried out under the full auspices of FDA-approved "Good Clinical Practices".

EXAMPLE 3

LYOPHILIZATION OF 10% FDP SOLUTION

After realizing that FDP's potential as a useful drug has been ignored and neglected by pharmaceutical manufacturers, the Applicant, Cypros Pharmaceutical Corporation, commenced a program of developing a suitable lyophilization procedure, to generate a stable and sterile preparation that can be stored for weeks or months and then mixed with water and injected into humans.

This preparation began with a non-sterile bulk powder, manufactured by Boehringer-Mannheim, in Germany. This powder is purchased as a tri-sodium salt. The crystalline form is an octahydrate, with eight molecules of water associated with each molecule of FDP. Calculated water comprises 26.18%, by weight, of this octahydrate salt. Although the concept of "water of hydration" (i.e., the water that remains bound to the FDP when it is in crystalline form) becomes irrelevant after FDP is dissolved in water, a reduction of the water content below 26%, in a lyophilized preparation, requires removal of at least a portion of the water that would remain bound if the FDP were in a normal crystallized form.

During the freezing process, if the FDP forms a glass (i.e., a solid that does not have a regular molecular lattice structure), there will be "sorbed" or "bound" water associated with the non-crystalline material. Such water can be removed by lyophilization. If the product (or some portion thereof) crystallizes during freezing, the product may be an octahydrate or some other hydrated crystalline form, and it is very difficult to remove such water by conventional lyophilization techniques, without melting or altering the crystals.

The bulk powder described above was thoroughly dissolved in water, at varying concentrations starting at about 10% by weight, and ranging up to about 40% by weight. The liquid was pumped through a Gelman "Acrodisc 50" filter with a pore size of 0.2 microns. This sub-micron filtering serves as a sterilization step which removes any bacteria or viral particles. No excipients were added, and the pH was not adjusted.

Filtered sterile solutions were filled into 100 mL molded glass vials. Varying amounts of liquid were loaded into each vial, depending on the concentration of the liquid, to create final quantities of 5 grams of FDP (octahydrate salt) in each vial throughout the tests described herein.

Permeable lyophilization stoppers were placed on the vials, and the vials were loaded onto the shelves in a lyophilization chamber (manufactured by The Virtis Company, Inc., Gardiner, N.Y.) at 13° C. Temperature probes were placed in four interior vials on each shelf.

All lyophilizations described in the Examples herein used the same lyophilization chamber, the same supplies (vials, lyophilization stoppers, aluminum stoppers, inert atmospheres, etc.), and the same analytical methods (temperature probes in internal vials, analytical tests, etc.). In some of the mixtures that were treated, temperature and vacuum conditions were varied somewhat, depending on the percentage FDP that was present in the mixture.

The following parameters describes lyophilization of a liquid containing 10% FDP, measured as the weight of the octahydrate salt. This was a very conservative approach, evaluated during an early stage of the research. In addition, these times were high, because of the relatively deep quantity of solution required for 10 or 20% FDP in aqueous solution. Subsequent tests involving 30 or 40% solutions of FDP used shallower liquid depths, and were tested more aggressively, using substantially shorter times.

The shelves were initially cooled to −45° C. in 56 minutes, and then cooled further, to −67° C., over five hours. Vacuum was initiated, and when the pressure reached 250 millitorr (mtorr), the shelf temperature was raised to −40° C. and maintained there for 162 hours. The shelf temperature was maintained between −20° C. and −40° C. for an additional 240 hours, and then raised to 10° C. for 15 hours. The temperature was then adjusted to 20° C. for 5 hours. Pressure was maintained between 50 and 100 mtorr throughout the cycle.

After this drying cycle was completed, the vacuum was released, and nitrogen or argon was bled into the lyophilization chamber. The vials were sealed inside the lyophilizer under an atmosphere of inert gas, at atmospheric pressure. Aluminum overseals were placed on the vials and crimped into place. This generated a dried cake mass which contained about 14% water, by weight.

The stability of this product was determined from real time stability studies, using high performance liquid chromatography (HPLC) analysis on a "CarboPac PA1" column (Dionex Corp. Sunnyvale, Calif.) using a Beckman pump and controller (Beckman Company, Fullerton, Calif.) with a Waters model 464 Pulsed Amperometric Detector (Waters Company, Milford, Mass.). The shelf life was found to be at least 14 months when the product was stored at room temperature (25° C. or lower).

It should be noted that the preparations described herein were not completely sterile. Although the liquids were sterile-filtered after the FDP power was dissolved in water, the powders and the vials were not handled under completely sterile conditions, in the lab-scale research which led to this invention. Accordingly, the excellent levels of chemical stability disclosed herein should be regarded as having an extra margin of safety; these stability levels were achieved despite a significant risk of biological contamination due to the non-sterile lab-scale handling procedures.

EXAMPLE 4

LYOPHILIZATION OF 20% FDP SOLUTION

FDP (400 g of bulk powder, sodium salt including octahydrate water) was dissolved in 2 liters of water. The solution was pumped through a Gelman Acrodisc 0.2 micron filter, as above, and filled into the vials (about 25 mL of solution/vial). The vials were loaded onto the lyophilizer shelves at 0° C. The shelves were cooled to −40° C. in ten hours and maintained at −40° C. over 1.75 hours. The shelf temperature was then raised to −18° C. over 4.75 hours and then lowered to −64° C. in two hours. Vacuum was then initiated. The shelf temperature was raised to −30° C. and maintained there for nine and a half days. The shelf temperature was then raised to 20° C. over 8.5 hours, and then maintained there for 19.5 hours. The pressure was maintained between 4 and 70 mtorr throughout the cycle. The vacuum was released, and the vials were sealed at atmospheric pressure.

This cake had a residual moisture content of 11.9%. HPLC analysis of a sample that had been stored at room temperature for 343 days indicated 0.8% total impurities.

EXAMPLE 5

LYOPHILIZATION OF 30% FDP SOLUTION

FDP (420 g of bulk powder) was dissolved in 1.4 liters of water (1.4 L), and pumped through the filter. 17 mL of solution was loaded into each vial. The solution depth was about 14 mm, measured next to the wall; depths in the middle of the vial were shallower. The vials were loaded onto the lyophilizer shelves at −55° C. The shelves were cooled to −67° C. and vacuum was initiated when the product temperature reached −65° C. When the pressure reached 16 mtorr the shelf temperature was raised to −15° C. and maintained there for 36 hours. The shelf temperature was then raised to 20° C. over 30 minutes and then maintained there for three and a half hours. The pressure was below 100 mtorr throughout the cycle. The vacuum was released, and the vials were sealed at atmospheric pressure.

This produced a cake with a residual moisture content of 14.5%. Analysis of a sample that had been stored at room temperature for 201 days indicated 0.7% total impurities.

EXAMPLE 6

LYOPHILIZATION OF 40% FDP SOLUTION, WITHOUT TBA

FDP (420 g) was dissolved in water (1.05 L) and pumped through the filter. 12.5 mL was loaded into each vial (depth next to wall was about 11 mm), and the vials were loaded onto the lyophilizer shelves at −57° C. The shelves were cooled to −70° C. and vacuum was initiated when the product temperature reached −68° C. The shelves were allowed to warm to −45° C. during vacuum pull-down, and when the pressure reached 71 mtorr the shelf temperature was raised to −10° C. over 1.25 hours and maintained there for 20 hours. The shelf temperature was then raised to 23° C. over 30 minutes and then maintained there for 19 hours. The pressure was below 100 mtorr throughout the cycle. The vacuum was released and the vials were sealed at atmospheric pressure.

The resulting cake collapsed, and was a pale yellow color. It was regarded as unacceptable, and was not analyzed for impurities. Instead, attention was turned to testing TBA as an agent to promote proper lyophilization, as described below.

EXAMPLE 7

LYOPHILIZATION OF 40% FDP SOLUTION WITH 10% TBA

Tertiary butyl alcohol (105 mL) was mixed with 600 mL of water. FDP (420 g) was dissolved in the mixture, then enough water was added to this mixture to give a final volume of 1050 mL. In other tests, TBA was added to the water after the FDP had been added; the sequence of mixing did not make any apparent difference.

The solution was pumped through the filter, and 12.5 mL aliquots were loaded into the 100 mL vials. The vials were loaded onto the lyophilizer shelves at 2.5° C. The shelves were cooled to −67° C. over 110 minutes and vacuum was initiated when the product temperature reached −60° C. The shelves were allowed to warm to −45° C. during vacuum pull-down and maintained for one-half hour. The shelf temperature was raised to −10° C. over 68 minutes and maintained there for 20 hours. The shelf temperature was then raised to 23° C. over 30 minutes and then maintained there for 17 hours. The pressure was below 110 mtorr throughout the cycle. The vacuum was released, and the vials were sealed.

This produced a fragile cake with multiple cracks, which broke apart and produced a powder when shaken. Residual water content was 13.2%, and HPLC showed 0.1% total impurities after 15 days at room temperature.

The major apparent differences which resulted when TBA was used, in a number of tests, involved the structure and color of the cake. With a 100% aqueous formulation, resulting FDP cakes tend to be relatively dense and hard, and were sometimes off-white or slightly yellow. When TBA was used, the cakes were substantially lighter in color, approaching a pure, bright white. They are also less dense and more fragile, and sometimes broke into powders if shaken vigorously.

The preparations above, using 30% or 40% FDP and TBA in the aqueous mixture, produced partially lyophilized preparations of FDP which appeared to have very good quality. These were prepared only recently; accordingly, extended data on shelf life is not yet available, but initial results appear to be very good.

Except as noted above, these preparations, including some that were prepared without TBA and some that were prepared with TBA, are believed to be completely suitable for reconstitution and injection into humans who need emergency treatment for an ischemic or hypoxic crisis, or who need various other forms of medical treatment by physicians.

Thus, there has been shown and described a new and useful method for preparing partially lyophilized forms of FDP for injection into human patients. There have also been shown certain chemical compositions that result from this lyophilization method, and certain articles of manufacture which contain partially lyophilized FDP as a key component. Although the processing method, chemical compositions, and articles of manufacture described herein have all been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Angelos, M. G., et al, "Fructose-1,6-diphosphate fails to limit early myocardial infarction size in a canine model," *Ann. Emerg. Med.* 22: 171–177 (1993)

Bickler, P. E., et al, "Fructose-1,6-bisphosphate stabilizes brain intracellular calcium during hypoxia in rats," *Stroke* 23: 1617–22 (1992)

Brunswick, R., et al, "Preservation of myocardium by infusion of fructose diphosphate following coronary occlusion," *Am J Cardiol* 49: 1008 (1982)

Cacioli, D., et al, "Haemorheological effects of fructose-1, 6diphosphate in patients with lower extremity ischaemia," *Curr Med Res Opin* 10: 668–74 (1988)

Cargnoni, A., et al, "Role of timing of administration in the cardioprotective effect of fructose-1,6-bisphosphate," *Cardiovasc Drugs Ther* 6: 209–17 (1992)

Crescimanno, M., et al, "Influence of fructose 1,6-diphosphate on the lung antioxidant defenses of mice with endotoxemia," *Pharmacol Res* 22: 74–75 (1990)

de la Torre, J. C. "Treatment of head injury in mice, using a fructose 1,6-diphosphate and dimethyl sulfoxide combination," *Neurosurgery* 37: 273–9 (1995)

Eddy, L. J., et al, "Lack of a direct metabolic effect of fructose, 1,6-diphosphate in ischemic myocardium," *Am J Physiol* 241: H576–83 (1995)

Farias, L. A., et al, "Prevention of ischemic-hypoxic brain injury and death in rabbits with fructose-1,6-diphosphate," *Stroke* 21: 606–13 (1990)

Farias, L. A., et al, "Effects of fructose-1,6-diphosphate, glucose and saline on cardiac resuscitation," *Anesthesiology* 65: 595–601 (1966)

Farias, L. A., et al, "Improved brain metabolism with fructose 1–6 diphosphate during insulin-induced hypoglycemic coma," Central University of Venezuela. *Am J Med Sci* 297: 294–9 (1989)

Galzigna, L., et al, "Some effects of FDP on rat myocardial tissue relate to a membrane stabilizing action," *Cell Biochem. Function* 7: 91–96 (1989)

Gobbel, G. T., et al, "Response of cerebral endothelial cells to hypoxia: modification by fructose-1,6-bisphosphate but not glutamate receptor antagonists," *Brain Res* 653: 23–30 (1994)

Grandi, A. M., et al, "Improved left ventricular function after short-term treatment with fructose-1,6-diphosphate," *Clin Ther* 10: 372–80 (1988)

Granot, H., et al, "Successful treatment of irreversible hemorrhagic shock in dogs with fructose-1,6diphosphate and dichloroacetate," *Circ Shock* 163–73 (1985)

Gregory, G. A., et al, "Fructose-1,6-bisphosphate reduces ATP loss from hypoxic astrocytes," *Brain Res* 516: 310–2 (1990)

Hardin, C. D., et al, "Metabolism of exogenously applied fructose 1,6-bisphosphate in hypoxic vascular smooth muscle," *Am J Physiol* 267: H2325–32 (1994)

Hassinen, I. E., et al, "Mechanism of the effect of exogenous fructose 1,6-bisphosphate on myocardial energy metabolism," *Circulation* 83: 584–93 (1991)

Janz, T. G., et al, "The effects of fructose-1,6-diphosphate on myocardial damage in acute coronary artery occlusion," *Resuscitation* 22: 45–54 (1991)

Kelleher, J. A., et al, "Energy metabolism in hypoxic astrocytes: protective mechanism of fructose-1,6-bisphosphate," *Neurochem Res* 20: 785–92 (1995)

Kuluz, J., et al, "Fructose-1,6-bisphosphate reduces infarct volume after reversible middle cerebral artery occlusion in rats," *Stroke* 24: 1576–83 (1993)

Lazzarino, G., et al, "Ischemia and reperfusion: effect of fructose-1,6-bisphosphate," *Free Radic Res Commun* 16: 325–39 (1992)

Lazzarino G., et al, "Protective effects of exogenously administered fructose-1,6-diphosphate from ischemia reperfusion damage induced on isolated rat heart," *Ital J Biochem* 38: 251A–253A (1989)

Marchionni, N., et al, "Hemodynamic and electrocardiographic effects of fructose-1,6-diphosphate in acute myocardial infarction," *Am J Cardiol* 56: 266–269 (1985)

Marchionni, N., et al, "Improved exercise tolerance by i.v. fructose-1,6-diphosphate in chronic, stable angina pectoris," *J Clin Pharmacol* 28: 807–11 (1988)

Markov, A. K., et al, "Hemodynamic, electrocardiographic, and metabolic effects of fructose diphosphate on acute myocardial ischemia," *Am Heart J* 100: 639–46 (1980)

Markov, A. K., "Hemodynamics and metabolic effects of fructose 1–6diphosphate in ischemia and shock-experimental and clinical observations," *Ann Emerg Med* 15: 1470–7 (1986)

Markov, A. K., et al, "Increasing survival of dogs subjected to hemorrhagic shock by administration of fructose 1–6diphosphate," *Surgery* 102: 515–27 (1987)

Munger, M. A., et al, "Effect of intravenous fructose-1,6-diphosphate on myocardial contractility in patients with left ventricular dysfunction," *Pharmacotherapy* 14: 522–8 (1994)

Myers, J., et al, "Effect of fructose-1,6-diphosphate on exercise capacity in patients with peripheral vascular disease," *Int J Sports Med* 11: 259–262 (1990)

Nakai, T., et al, "Beneficial effects of fructose-1,6-diphosphate infusion on liver regeneration after ischemic liver injury," *Gastroenterology Japan* 26: 611–8 (1991)

Pasque, M. K., et a, "Metabolic intervention to affect myocardial recovery following ischemia," *Annals of Surgery* 200: 1–12 (1984)

Sano, W., et al, "Beneficial effect of fructose-1,6-bisphosphate on mitochondrial function during ischemia-reperfusion of rat liver," *Gastroenterology* 108: 1785–92 (1995)

Tortosa, A., et al, "Fructose-1,6-bisphosphate fails to ameliorate delayed neuronal death in the CA1 area after transient forebrain ischaemia in gerbils," *Neuropharmacology* 32: 1367–71 (1992)

Trimarchi, G. R., et al, "Neuroprotective activity of fructose-1,6-bisphosphate following transient forebrain ischemia in the Mongolian gerbil," *Japan J Pharmacol* 62: 215–22 (1993)

Trimarchi, G. R., et al, "Effects of fructose-1,6-bisphosphate on brain polyamine biosynthesis in a model of transient cerebral ischemia," *Life Sci* 54: 1195–204 (1994)

Zhang, J. N., et al, "Protective effect of exogenous fructose-1,6-diphosphate in cardiogenic shock," *Cardiovasc Res* 22: 927–32 (1988)

I claim:

1. A method of preparing a partially lyophilized formulation of fructose-1,6-diphosphate which is sterile, chemically stable, and suitable for reconstitution with an aqueous solution and injection into humans, comprising the following steps:

(a) creating an aqueous solution containing fructose-1,6-diphosphate;

(b) loading a predetermined quantity of the aqueous solution into a sterilized vial designed to hold the fructose-1,6-diphosphate in a sealed enclosure after lyophilization;

(c) placing the vial which contains the predetermined quantity of aqueous solution in a lyophilization chamber;

(d) reducing the temperature in the lyophilization chamber to below the glass transition temperature of fructose-1,6-diphosphate, to create a frozen solid mixture in the vial;

(e) subjecting the frozen solid mixture to a drying process in which suitable vacuum and cold temperature conditions are sustained for a sufficient time to cause water molecules to sublimate from the frozen solid mixture, until a desired quantity of residual water remains, thereby generating a fructose-1,6-diphosphate mass comprising between 10% and 25% water, by weight;

(f) sealing the vial in a watertight manner while the vial remains under sterile conditions, thereby enclosing the fructose-1,6-diphosphate mass inside a sealed watertight vial, wherein all such processing is carried out under sterile conditions, thereby generating a sealed and sterile preparation of partially lyophilized fructose-1,6-diphosphate which is chemically stable and which will not suffer chemical degradation which generates more than 5 percent total impurities or more than 1 percent for any single impurity over a span of 1 month when stored at 25° C. in the sealed vial, and which can be reconstituted, by mixing the partially lyophilized fructose-1,6-diphosphate mass with an aqueous solution, to generate an aqueous pharmaceutical preparation that is suitable for injection into humans.

2. The method of claim 1, wherein the aqueous solution contains about 10% to about 40% fructose-1,6-diphosphate, by weight.

3. The method of claim 1, wherein the aqueous solution is sterilized by passing it through a sterilizing filter before the aqueous solution is loaded into the vial.

4. The method of claim 1, wherein the aqueous solution containing fructose-1,6-diphosphate also contains a second agent which sublimates readily at −40° C.

5. The method of claim 4, wherein the second agent comprises tertiary-butyl alcohol.

6. An article of manufacture, comprising a sterile and partially lyophilized preparation of fructose-1,6-diphosphate, prepared by the method of claim 1, in a unit-dosage quantity which is suitable for reconstitution with an aqueous solution for intravenous infection of the fructose-1,6-diphosphate into a human patient in a single bolus injection, and a sealed watertight vial which encloses the partially lyophilized preparation of fructose-1,6-diphosphate and maintains its sterility.

7. An article of manufacture, comprising a sterile and partially lyophilized preparation of fructose-1,6-diphosphate, prepared by the method of claim 5, in a unit-dosage quantity which is suitable for reconstitution with an aqueous solution for intravenous injection of the fructose-1,6-diphosphate into a human patient in a single bolus injection, and a sealed watertight vial which encloses the partially lyophilized preparation of fructose-1,6-diphosphate and maintains its sterility.

8. A method of preparing chemically stable fructose-1,6-diphosphate which has been subjected to lyophilization, comprising the following steps:

(a) placing a quantity of aqueous solution containing fructose-1,6-diphosphate inside an open vial that can be sealed in a sterile manner;

(b) lyophilizing the aqueous solution in the vial, under suitable freezing and vacuum conditions in a lyophilization chamber, until a sufficient quantity of water has been removed to generate a solidified fructose-1,6-diphosphate mass which contains between about 10% and about 25% residual moisture content, by weight; and, (c) sealing the vial in a watertight manner;

wherein all such steps are carried out under sterile conditions, thereby generating a sterile preparation of solidified fructose-1,6-diphosphate which is sufficiently chemically stable so that, after one month of storage in the vial at room temperature, it will contain less than 5 percent total impurities, by weight and contain less than 1 percent of any single impurity, by weight.

9. The method of claim 8, wherein the aqueous solution contains about 10% to about 40% fructose-1,6-diphosphate, by weight.

10. The method of claim 8, wherein the aqueous solution is sterilized by passing it through a sterilizing filter before the aqueous solution is loaded into the vial.

11. The method of claim 8, wherein the aqueous solution containing fructose-1,6-diphosphate also contains a second agent which sublimates readily at −40° C.

12. The method of claim 11, wherein the second agent comprises tertiary-butyl alcohol.

13. The method of claim 8, wherein the solidified fructose-1,6-diphosphate comprises a caked mass.

14. The method of claim 8, wherein the solidified fructose-1,6-diphosphate comprises a powdered mass.

15. An article of manufacture, comprising a solidified formulation of fructose-1,6-diphosphate, prepared by the method of claim 8, in a unit-dosage quantity which is suitable for reconstitution with an aqueous solution for intravenous injection of the fructose-1,6-diphosphate into a human patient in a single bolus injection, and a sealed watertight vial which encloses the partially lyophilized preparation of fructose-1,6-diphosphate and maintains its sterility.

16. An article of manufacture, comprising a solidified formulation of fructose-1,6-diphosphate, prepared by the method of claim 12, in a unit-dosage quantity which is suitable for reconstitution with an aqueous solution for intravenous injection of the fructose-1,6-diphosphate into a human patient in a single bolus injection, and a sealed watertight vial which encloses the partially lyophilized preparation of fructose-1,6-diphosphate and maintains its sterility.

17. An article of manufacture, comprising a sealed watertight vial and a solidified formulation of fructose-1,6-diphosphate, wherein:

a. the fructose-1,6-diphosphate contains between 10% and 25% water, by weight;

b. the fructose-1,6-diphosphate is sterile and free of any viruses or bacteria;

c. the fructose-1,6-diphosphate contains less than 5 percent total impurities, by weight, and contains less than 1 percent of any single impurity, by weight; and, d. the fructose-1,6-diphosphate is suitable for mixing with an aqueous solution, to generate an aqueous pharmaceutical preparation of fructose-1,6-diphosphate for injection into humans, and wherein the sealed watertight vial encloses the partially lyophilized preparation of fructose-1,6-diphosphate and maintains its sterility.

18. The article of manufacture of claim 17, wherein the solidified formulation of fructose-1,6-diphosphate has sufficient chemical stability so that it will contain less than 5 percent total impurities, by weight, and less than 1 percent of any single impurity, by weight, after at least one month of storage at room temperature.

* * * * *